United States Patent [19]

Amato et al.

[11] Patent Number: 5,362,862
[45] Date of Patent: Nov. 8, 1994

[54] PROCESS FOR 4″-EPI-ACETYLAMINO-4″-DEOXY-5-OXIMINOAVERMECTIN-B$_1$

[75] Inventors: Joseph S. Amato, Brooklyn, N.Y.; Raymond Cvetovich, Scotch Plains, N.J.

[73] Assignee: Merck & Co., Inc., Rahway, N.J.

[21] Appl. No.: 128,935

[22] Filed: Sep. 29, 1993

[51] Int. Cl.$^5$ .................. C07H 17/04; A61K 31/70
[52] U.S. Cl. ......................................... 536/7.1; 514/30
[58] Field of Search ................ 536/7.1; 514/30, 450; 549/264

[56] References Cited

U.S. PATENT DOCUMENTS

| | | | |
|---|---|---|---|
| 4,427,663 | 1/1984 | Mrozik | 424/180 |
| 4,547,520 | 10/1985 | Ide et al. | 514/450 |
| 5,015,630 | 5/1991 | Fisher et al. | 514/30 |
| 5,023,241 | 6/1991 | Linn et al. | 514/30 |

FOREIGN PATENT DOCUMENTS

| | | |
|---|---|---|
| 0379341 | 1/1990 | European Pat. Off. . |
| 0411897 | 7/1990 | European Pat. Off. . |
| 0519731 | 6/1992 | European Pat. Off. . |

OTHER PUBLICATIONS

Tetrahedron Letter, No. 45, pp. 4313–4316 (1971), by T. M. Chau, et al.
Agri & Biol. Chem. vol. 55 (10), pp. 2615–2621 (1991) by Y. Tsukamoto, et al.

*Primary Examiner*—Johnnie R. Brown
*Assistant Examiner*—Howard C. Lee
*Attorney, Agent, or Firm*—David L. Rose; Joseph F. DiPrima

[57] ABSTRACT

An improved process for formation of a 5-oxime on avermectin derivatives comprises the treatment of the oxo compound with O-(trimethylsilyl)hydroxylamine in the presence of a Lewis acid.

1 Claim, No Drawings

PROCESS FOR 4"-EPI-ACETYLAMINO-4"-DEOXY-5-OXIMINOAVERMECTIN-B₁

BACKGROUND OF THE INVENTION

The avermectins are a unique collection of naturally occurring macrocyclic lactones containing an α-L-oleandrosyl-α-L-oleandrose disaccharide appended to the $C_{13}$-hydroxyl group of the aglycone unit, and exhibit anthelmintic and insecticidal properties. Since the introduction and expanded use of 'abamectin' for the control of a variety of agricultural pests, and the subsequent commercialization of 'ivermectin' in the animal health area including the use of 'MECTIZAN' for the control of riverblindness in humans, a large number of avermectin derivatives have been synthesized seeking potential increases in the spectrum of parasite control in plants, animals and humans. Among these new analogues is 4"-epi-acetylamino-4"-deoxy-5-oximino-avermectin $B_1$. This derivative has attracted attention for the control of internal parasites in companion animals and its efficient preparation in large quantity is commercially important. This compound is described in U.S. Pat. Nos. 5,015,630 and 5,023,241 being prepared by treatment of the 5-oxo compound with hydroxylamine in the presence of base which produced mainly the 3-hydroxylamino-5-oximino analog as a by-product.

SUMMARY OF THE INVENTION

This invention is concerned with an improved process for the preparation of 5-oximinoavermectin $B_1$ analogs, particularly 4"-epi-acetylamino-4"-deoxy-5-oximinoavermectin $B_1$. The process comprises the treatment of the corresponding 5-oxo starting material with O-(trimethylsilyl)hydroxylamine in the presence of a Lewis acid. These conditions provide yields of about 90% with no hydrolysis of the terminal saccharide nor production of a 3-hydroxylamino by-product formed by addition of hydroxylamine across the 3, 4 double bond.

DETAILED DESCRIPTION OF THE INVENTION

The novel process of this invention comprises the preparation of the compound of structural formula I:

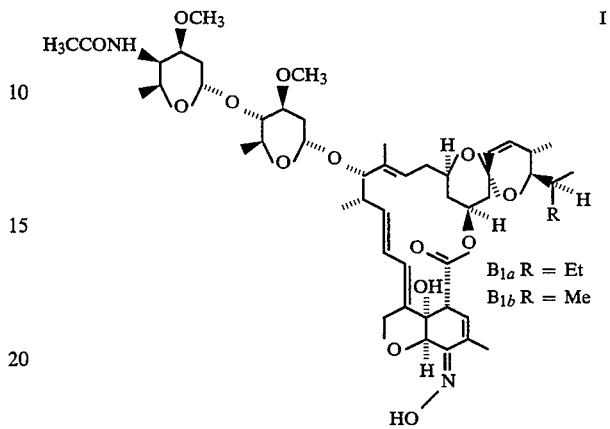

$B_{1a}$ R = Et
$B_{1b}$ R = Me by treating the compound of structural formula III:

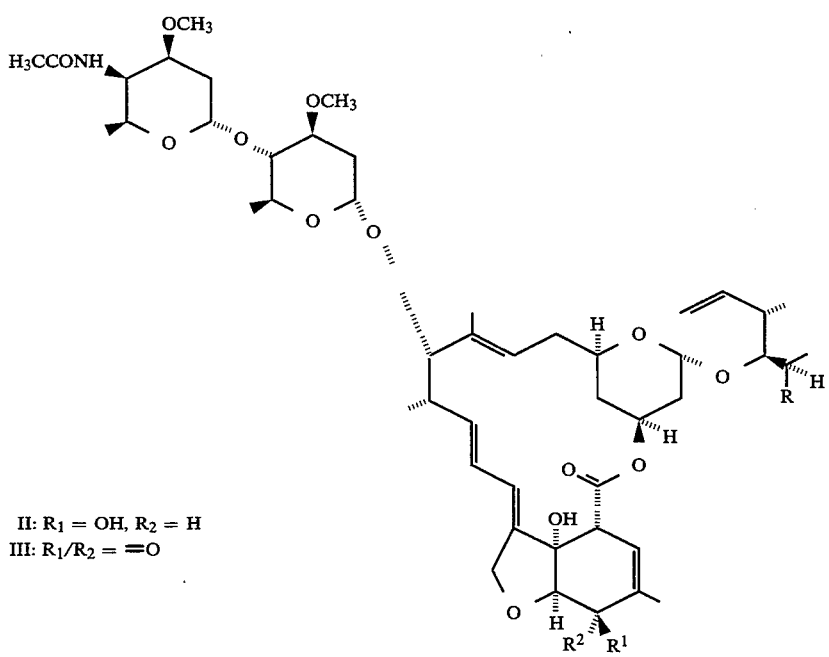

II: $R_1$ = OH, $R_2$ = H
III: $R_1/R_2$ = =O in an organic solvent with O-(trimethylsilyl)hydroxylamine in the presence of a Lewis acid.

The organic solvent is preferably isopropyl acetate (IPOAc).

The concentration of III in the solvent is not critical but is usually about 3–6 ml of IPOAc/gm of III.

A 2–4 molar excess of O-(trimethylsilyl)hydroxylamine and of Lewis acid is employed in the novel process.

The Lewis acid useful in the novel process is zinc chloride, zinc bromide or the like, preferably zinc chloride.

The temperature at which the process is conducted also is not critical but temperatures of about 15° to 30° C. are appropriate; room temperature being most convenient.

Oximation of enone III was expected to result from the usual conditions of hydroxylamine hydrochloride in the presence of base. Oximation of III by the action of hydroxylamine hydrochloride in the presence of pyridine or diisopropylethylamine led to poor yields (30–60%) of oxime I. The major by-product found from these reactions was the 3-hydroxylamino-5-oxime, IV.

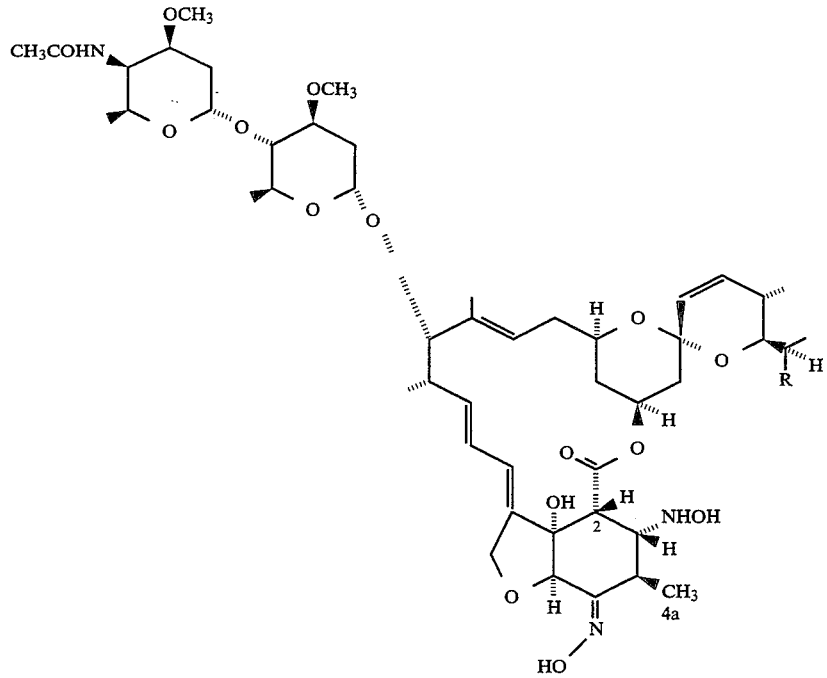

In attempts to modify the reactivity of hydroxylamine and minimize the formation of the 3-hydroxylamino-5-oxime, the action of O-(trimethylsilyl)hydroxylamine was examined in non-aqueous systems. With no added base other than excess O-(trimethylsilyl)hydroxylamine, little or no oxime formation was detected. Because rates of oxime formation using hydroxylamine are known to be sensitive to acid or base, oximation in the presence of a Lewis acid was explored. Oximation of α,β-unsaturated ketone II with O-(trimethylsilyl)hydroxylamine/ZnCl$_2$ in isopropyl acetate followed by a hydrolytic workup with 5% aqueous phosphoric acid gave oxime I in 90% yield.

NMR experiments (NOE) have determined that the major stereochemical orientation of the oxime is as the Z-isomer, 1-Z.

The compound of this invention has significant parasiticidal activity as an anthelmintic, ectoparasiticide, insecticide, and acaracide, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and often serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictocaulus, Capillaria, Heterakis, Toxocara, Ascaridia, Oxyuris, Ancylostoma, Uncinaria, Toxascaris, and Parascaris. Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The avermectin compound of this invention has unexpectedly high activity against Dirofilaria in dogs, Nematospiroides, Syphacia, Aspiculuris in rodents, anthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

This compound may be administered orally in a unit dosage form such as a capsule, bolus or tablet, or as a liquid drench where used as an antheimintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 5% by weight of the active compound. Preferred drench formulations may contain from 0.001 to 0.1% by weight active compound. The capsules or boluses are comprised of the active ingredient admixed with a carrier vehicle such as starch, talc, magnesium stearate, or di-calcium phosphate.

Where it is desired to administer the avermectin derivative in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be administered via the animal feedstuff, it is intimately dispersed in the feed or used as a top dressing or in the form of pellets which may then be added to the finished feed or optionally fed separately. Alternatively, the antiparasitic compound of this invention may be administered to the animals parenterally, for example, by intramminal, intramusucular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other parenteral vehicles such as organic preparations using solketal, glycerol formal, and aqueous parenteral formulations are also used. The active avermectin compound or compounds are dissolved or suspended in the parenteral formulation for administration; such formulations generally contain from 0.005 to 5% by weight of the active compound. The optimum amount to be employed will, of course, depend upon the particular compound employed, the species of animal to be treated and the type and severity of parasitic infection or infestation. Generally good results are obtained with this compound by the oral administration of from about 0.001 to 10 mg per kg of animal body weight, such total dose being given at one time or in divided doses over a relatively short period of time such as 1-5 days. Generally, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering this material to animals are known to those skilled in the veterinary field. When the compound described herein is administered as a component of the feed of the animals, or dissolved or suspended in the drinking water, compositions are provided in which the active compound is intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compound is intimately dispersed throughout the carrier by methods such as grinding, stirring, milling, or tumbling. Compositions containing from about 0.005 to 2.0% by weight of the active compound are particularly suitable as feed premixes. Feed supplements, which are fed directly to the animal, contain from about 0.002 to 0.3% by weight of the active compound.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compound of this invention is usually fed at concentrations of between 0.00001 to 0.002% in the feed in order to achieve the desired antiparasitic result.

EXPERIMENTAL

GENERAL

HPLC analyses were performed using a Spectra-Physics SP8700 ternary solvent delivery system with a Vydac C18 Protein/Peptide (218TP54) reverse phase column, at 25° C., UV detection at 245 nm, with the solvent systems described in each experimental. All reactions were carried out under an atmosphere of $N_2$, and the solvents and reagents were used as received or were dried over 3Å molecular sieves prior to use as needed. Karl Fisher water analyses were performed with a Metrohm 684 KF Coulometer. Infrared spectra were recorded on a Perkin-Elmer 1420 Ratio Recording Infrared Spectrophotometer. Melting points were determined using a DuPont 9900 DSC (2° C./min, under $N_2$ in an open cup) and are reported as a range from the DSC extrapolated onset temperature to the peak temperature. Proton and carbon-13 spectra were recorded in CDC13 on a Bruker AM-400 at a frequency of 400.13 and 100.61 MHz, resp. The chemical shifts are reported in ppm relative to residual $CHCl_3$ for proton ($\delta=7.27$ ppm) and $CDCl_3$ for carbon ($\delta=77.0$ ppm). All coupling constants are reported in Hz and the following proton multiplicites are abbreviated as follows: s=singlet, d=doublet, t=triplet, q=quartet, m=multiplet, om=overlapping multiplets, br=broad. High resolution mass spectroscopy studies were performed in the FAB mode. MK-397 was used as the mixture of $B_{1a}$ and $B_{1b}$ components.

EXAMPLE 1

4''-epi-Acetylamino-4''-Deoxy-5-oximino-avermectin $B_1$

Step A: Preparation of 4''-epi-Acetylamino-4''-5-oxo-Deoxyavermectin $B_1$

To a solution of 4''-epi-acetylamino-4''-deoxyavermectin $B_1$ (25.0 g, 25.8 mmol), DMSO (7.5 mL) and triethylamine (18.5 mL) in iPrOAc (175 mL) at $-20°$ C. was added phenyl dichlorophosphate (7.55 mL) over 30 min. After a 90 min age at $-10°$ C., the reaction was quenched with sat aq NaCl (100 mL), and the organic phase was washed with a 1:1 mixture of sat aq $NaHCO_3$ and sat aq NaCl (100 mL). The solvent was removed in vacuo (40° C., 28 in. Hg) to give III as a solid foam (24.6 g) which was used as is for the oximation steps. A sample was purified by silica gel chromatography (E. Merck Silica Gel 60, 230–400 mesh, 25% ethyl acetate/-hexanes). HPLC assay: gradient, acetonitrile:water (0.1% $H_3PO_4$), 50:50 to 90:10 over 30 min; (II) $t_R$:$B_{1b}$=5.18 min, $B_{1a}$=6.86 min; (III) $t_R$:$B_{1b}$=10.3 min, $B_{1a}$=12.4 min. $^1$H NMR:$\delta$ 6.58 (br s, $H_3$), 5.93 (dm, J=10.3, $H_9$), 5.82–5.69 (om, $H_{10}$, $H_{11}$, $H_{23}$), 5.60 (d, J=10.0, NH), 5.56 (dd, J=9.9, 2.5, $H_{22}$), 5.42 (m, $H_{19}$), 5.38 (d, J=3.8, $H_{1''}$), 4.98 (m, $H_{15}$), 4.78 (br d, J=3.1, $H_{1'}$), 4.73 (m, $C_{8a}H_2$), 4.44 (dd, J=10.0, 2.9, $H_{4''}$), 4.06 (m, $H_{5''}$), 4.02 (s, 7-OH), 3.94 (br s, $H_{13}$), 3.93–3.77 (om, $H_{17}$, $H_{5'}$), 3.85 (s, $H_6$), 3.71–3.57 (om, $H_2$, $H_{3'}$, $H_{3''}$), 3.48 (d, 9.5, $H_{25}$), 3.43, 3.39 (s's, 3'—OCH$_3$, 3''—OCH$_3$), 3.21 (t, J=9.0, $H_{4'}$), 2.53 (m, $H_{12}$), 2.37–2.18 (om, $C_{16}H_2$, $H_{24}$, $C_{2'}H_{eq}$), 2.06 (s, COCH$_3$), 2.06–2.00 (om, $C_{20}H_{eq}$, $C_{2''}H_{eq}$), 1.88 (s, $C_{4a}H_3$), 1.80 (m, $C_{18}H_{eq}$), 1.67–1.41 (om, $C_{20}H_{ax}$, $H_{26}$, $C_{27}H_2$, $C_{2'}H_{ax}$, $C_{2''}H_{ax}$), 1.49 (br s, $C_{14a}H_3$), 1.23 (d, J=6.2, $C_6'H_3$), 1.16 (d, J=6.7, $C_{12a}H_3$), 1.13 (d, J=6.5, $C_{6''}H_3$), 0.98–0.89 (om, $C_{18}H_{ax}$, $C_{24a}H_3$, $C_{26a}H_3$, $C_{28}H_3$). $^{13}$C NMR:δ 192.1 ($C_5$), 172.2 ($C_1$), 170.8 (CH$_3$CO), 139.0 ($C_{11}$), 138.1 ($C_3$), 137.9 ($C_8$), 136.8 ($C_4$), 136.4 ($C_{22}$), 135.2 ($C_{14}$), 127.5 ($C_{23}$), 124.6 ($C_{10}$), 121.8 ($C_9$), 118.1 ($C_{15}$), 98.7 ($C_{1''}$), 95.8 ($C_{21}$), 94.9 ($C_{1'}$), 82.0 ($C_{13}$), 81.9 ($C_7$), 81.0 ($C_{4'}$), 80.8 ($C_6$), 79.3 ($C_{3'}$), 74.9 ($C_{25}$), 73.3 ($C_{3''}$), 69.9 ($C_{8a}$), 69.1 ($C_{19}$), 68.4 ($C_{5'}$), 67.1 ($C_{17}$), 65.5 ($C_{5''}$), 56.4 (3'—OCH$_3$), 55.9 (3''—OCH$_3$), 48.4 ($C_{4''}$), 46.6 ($C_2$), 40.5 ($C_{20}$), 39.9 ($C_{12}$), 36.6 ($C_{18}$), 35.2 ($C_{26}$), 34.5 ($C_{16}$), 34.2 ($C_{2'}$), 31.9 ($C_{2''}$), 30.6 ($C_{24}$), 27.6 ($C_{27}$), 23.5 (CH$_3$CO), 20.1 ($C_{12a}$), 18.3 ($C_{6'}$), 17.1 ($C_{6''}$), 16.4 ($C_{24a}$), 15.5 ($C_{4a}$), 15.1 ($C_{14a}$), 13.0 ($C_{26a}$), 12.1 ($C_{28}$).

HRMS:[MH]$^+$=912.5087 (calculated=912.5108).

IR (CCl$_4$):λ$_{max}$=3440, 2980, 2940, 1735, 1712, 1685, 1500, 1450, 1370, 1120, 980 cm$^{-1}$.

Anal. Calcd for $C_{50}H_{73}NO_{14}$: C, 65.84; H, 8.07; N, 1.54.

Found: C, 65.85; H, 8.30; N, 1.90.

Step B: Preparation of 4''-epi-Acetylamino-4''-5-oximino-Deoxyavermectin B$_1$

To a solution of ketone III (23.4 g, 24.2 mmol) in iPrOAc (100 mL) was added ZnCl$_2$ (3.87 g, 28.4 mmol) and O-(trimethylsilyl)-hydroxylamine (4.9 mL, 39.7 mmol). The mixture was aged for 4 hours at 25° C. Sat aq NaCl (20 mL) and 5% aq phosphoric acid (20 mL) were added and the mixture was aged for 40 min. The organic phase was washed with a mixture of sat aq NaCl (20 mL) and sat aq NaHCO$_3$ (20 mL), then washed with sat aq NaCl (20 mL). The organic phase was concentrated in vacuo, and crystallized as above to give 18.7 g of I (80% yield), mp=185°–191° C. HPLC assay: gradient, acetonitrile:water (0.1% H$_3$PO$_4$), 50:50 to 88:12 over 15 min, 2.0 mL/min; (IV) B$_{1b}$:t$_R$=4.0 min, B$_{1a}$:t$_R$=4.76 min; (Ia) B$_{1b}$:t$_R$=7.95 min, B$_{1a}$:t$_R$=9.38 min; (Ib) B$_{1a}$:t$_R$=9.68 min; (3) B$_{1b}$:t$_R$=9.41 min, B$_{1a}$:t$_R$=10.89 min. $^1$H NMR:δ 8.93 (br, N—OH), 5.94 (m, H$_9$), 5.81 (m, H$_3$), 5.77 (dd, J=9.9, 1.6, H$_{23}$), 5.75 (om, H$_{10}$, H$_{11}$), 5.66 (d, J=9.9, NH), 5.56 (dd, J=9.9, 2.8, H$_{22}$), 5.44 (m, H$_{19}$), 5.39 (d, J=4.0, H$_{1''}$), 4.98 (br dd, J=9.5, 4.8, H$_{15}$), 4.80–4.66 (om, C$_{8a}$H$_2$, H$_{1'}$), 4.67 (s, H$_6$), 4.44 (dd, J=10.3, 3.6, H$_{4''}$), 4.07 (qd, J=6.3, 1.2, H$_{5''}$), 3.94 (br s, H$_{13}$), 3.87 (om, 7—OH, H$_{17}$, H$_{5'}$), 3.70 (m, H$_{3''}$), 3.63 (ddd, J=11.5, 8.7, 4.8, H$_{3'}$,), 3.49 (dd, 9.9, 1.2, H$_{25}$), 3.44 (s, 3'—OCH$_3$), 3.42 (m, H$_2$), 3.40 (s, 3''—OCH$_3$), 3.22 (t, J=9.1, H$_{4'}$), 2.53 (m, H$_{12}$), 2.35–2.20 (om, C$_{16}$H$_2$, H$_{24}$, C$_{2'}$H$_{eq}$), 2.07 (s, COCH$_3$), 2.03 (om, C$_{20}$H$_{eq}$, C$_{2''}$H$_{eq}$), 1.94 (dd, J=2.4, 1.2, C$_{4a}$H$_3$), 1.80 (m, C$_{18}$H$_{eq}$), 1.67–1.44 (om, C$_{20}$H$_{ax}$, H$_{26}$, C$_{27}$H$_2$, C$_{2'}$H$_{ax}$, C$_{2''}$H$_{ax}$), 1.50 (br s, C$_{14a}$H$_3$), 1.24 (d, J=6.3, C$_6'$H$_3$), 1.17 (d, J=6.7, C$_{12a}$H$_3$), 1.13 (d, J=6.3, C$_{6''}$H$_3$), 0.98–0.89 (om, C$_{24a}$H$_3$, C$_{26a}$H$_3$, C$_{28}$H$_3$), 0.89 (om, C$_{18}$H$_{ax}$). $^{13}$C NMR:δ 173.2 (C$_1$), 170.9 (CH$_3$CO), 151.4 (C$_5$), 138.2 (C$_8$), 138.1 (C$_{11}$), 136.3 (C$_{23}$), 135.1 (C$_{14}$), 132.2 (C$_4$), 127.7 (C$_{22}$), 125.0 (C$_3$), 124.9 (C$_{10}$), 121.3 (C$_9$), 118.3 (C$_{15}$), 98.7 (C$_{1''}$), 95.8 (C$_{21}$), 94.9 (C$_{1'}$), 82.0 (C$_{13}$), 81.1 (C$_{4'}$), 79.3 (C$_{3'}$), 78.6 (C$_7$), 74.9 (C$_{25}$), 73.3 (C$_{3''}$), 72.9 (C$_6$), 68.7 (C$_{8a}$), 68.5, 68.4 (C$_{17}$, C$_{19}$), 67.0 (C$_{5'}$), 65.5 (C$_{5''}$), 56.6 (3'-OMe), 56.1 (3''-OMe), 48.4 (C$_{4''}$), 46.4 (C$_2$), 40.5 (C$_{20}$), 39.9 (C$_{12}$), 6.6 (C$_{18}$), 35.2 (C$_{26}$), 34.5 (C$_{2'}$), 34.2 (C$_{16}$), 31.8 (C$_{2''}$), 30.6 (C$_{24}$), 27.5 (C$_{27}$), 23.4 (CH$_3$CO), 20.2 (C$_{12a}$), 18.3 (C$_{6'}$), 17.5 (C$_{4a}$), 17.0 (C$_{6''}$), 16.4 (C$_{24a}$), 15.1 (C$_{14a}$), 13.0 (C$_{26a}$), 12.0 (C$_{28}$).

HRMS:[M+Li]$^+$=933.5315 (calculated=933.5299).

IR (CHCl$_3$):λ$_{max}$=3660, 3450, 3010, 2990, 2940, 1710, 1665, 1505, 1450, 1370, 1340, 1190, 1120, 1050, 990 cm$^{-1}$.

Anal. Calcd for $C_{50}H_{74}N_2O_{14}$ and corrected for 5.8 wt % EtOH and 3.92 wt % H$_2$O: C, 62.0; H, 8.21; N, 2.81.

Found: C, 61.7; H, 8.55; N, 2.79.

What is claimed is:

1. A process for the preparation of the compound of structural formula I.

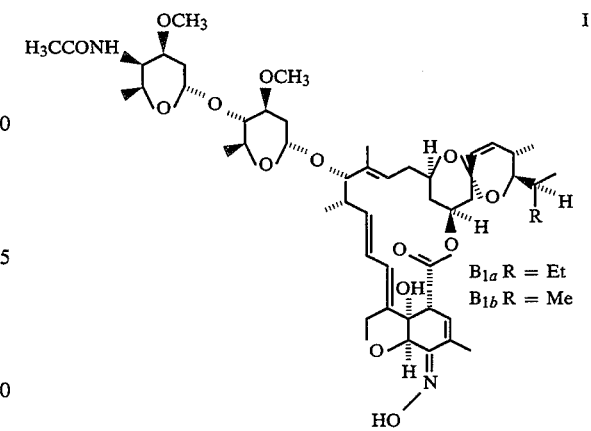

B$_{1a}$ R = Et
B$_{1b}$ R = Me which comprises the treatment of the compound of structural formula III:

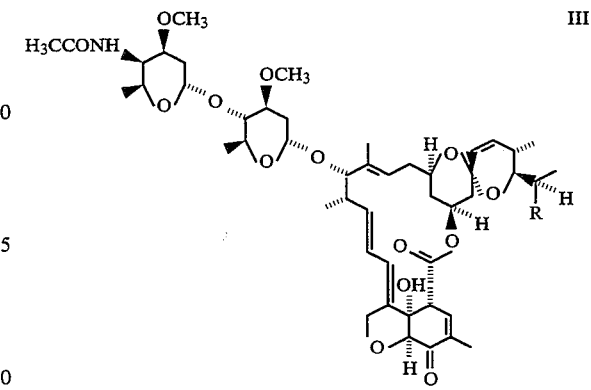

in isopropyl acetate with O-(trimethylsilyl)hydroxylamine in the presence of ZnCl$_2$.

* * * * *